United States Patent
Makihira et al.

(10) Patent No.: US 9,888,844 B2
(45) Date of Patent: *Feb. 13, 2018

(54) CONTROL APPARATUS AND CONTROL METHOD

(71) Applicant: CANON KABUSHIKI KAISHA, Tokyo (JP)

(72) Inventors: Tomoyuki Makihira, Tokyo (JP); Yoshihiko Iwase, Kyoto (JP); Makoto Sato, Tokyo (JP); Kazuhide Miyata, Yokohama (JP); Hiroyuki Shinbata, Tama (JP); Ritsuya Tomita, Kawasaki (JP); Daisuke Kibe, Chigasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,471

(22) Filed: Jan. 8, 2015

(65) Prior Publication Data
US 2015/0124262 A1    May 7, 2015

Related U.S. Application Data

(63) Continuation of application No. 13/742,987, filed on Jan. 16, 2013, now Pat. No. 8,960,909.

(30) Foreign Application Priority Data

Jan. 20, 2012    (JP) ................. 2012-010276

(51) Int. Cl.
*A61B 3/14*    (2006.01)
*A61B 3/10*    (2006.01)
(Continued)

(52) U.S. Cl.
CPC .............. *A61B 3/14* (2013.01); *A61B 3/0008* (2013.01); *A61B 3/102* (2013.01); *A61B 3/1225* (2013.01);
(Continued)

(58) Field of Classification Search
CPC ....... A61B 3/0075; A61B 3/14; A61B 3/1225; A61B 3/102; A61B 3/0008;
(Continued)

(56) References Cited

U.S. PATENT DOCUMENTS

| | | | |
|---|---|---|---|
| 8,960,909 B2 * | 2/2015 | Makihira | G01J 4/00 351/206 |
| 2007/0216866 A1 * | 9/2007 | Kobayashi | A61B 3/1015 351/221 |

(Continued)

FOREIGN PATENT DOCUMENTS

JP    2013-076587 A    4/2013

*Primary Examiner* — Jordan Schwartz
(74) *Attorney, Agent, or Firm* — Canon USA, Inc., IP Division

(57) ABSTRACT

A control apparatus includes an irradiation unit configured to irradiate a measurement object with a measuring beam, a restriction unit configured to restrict the measuring beam from being incident on the measurement object and to reflect or scatter the measuring beam, and a polarization control unit configured to control, based on the measuring beam reflected or scattered by the restriction unit, polarization of the measuring beam.

29 Claims, 6 Drawing Sheets

(51) Int. Cl.
   *G01B 9/02* (2006.01)
   *G01J 4/00* (2006.01)
   *A61B 3/00* (2006.01)
   *A61B 3/12* (2006.01)

(52) U.S. Cl.
   CPC ...... *G01B 9/02011* (2013.01); *G01B 9/02091* (2013.01); *G01J 4/00* (2013.01); *G01B 2290/70* (2013.01)

(58) Field of Classification Search
   CPC ............ G01B 9/02011; G01B 9/02091; G01B 2290/70; G01J 4/00
   USPC ......................................... 351/206–207, 215
   See application file for complete search history.

(56) References Cited

U.S. PATENT DOCUMENTS

| | | | | |
|---|---|---|---|---|
| 2011/0286003 A1* | 11/2011 | Ono | .................. | A61B 3/102 356/495 |
| 2012/0293770 A1* | 11/2012 | Hirose | ................ | A61B 3/1025 351/206 |

* cited by examiner

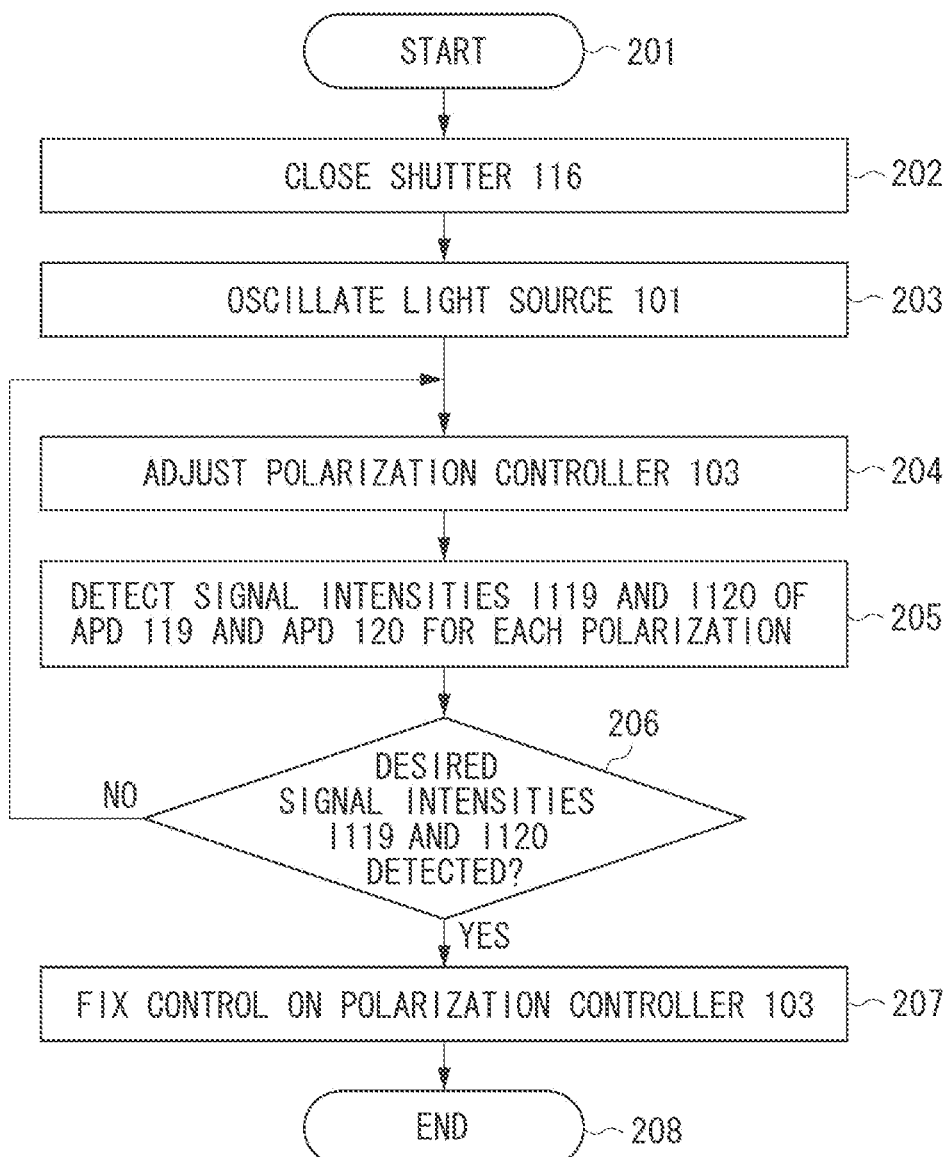

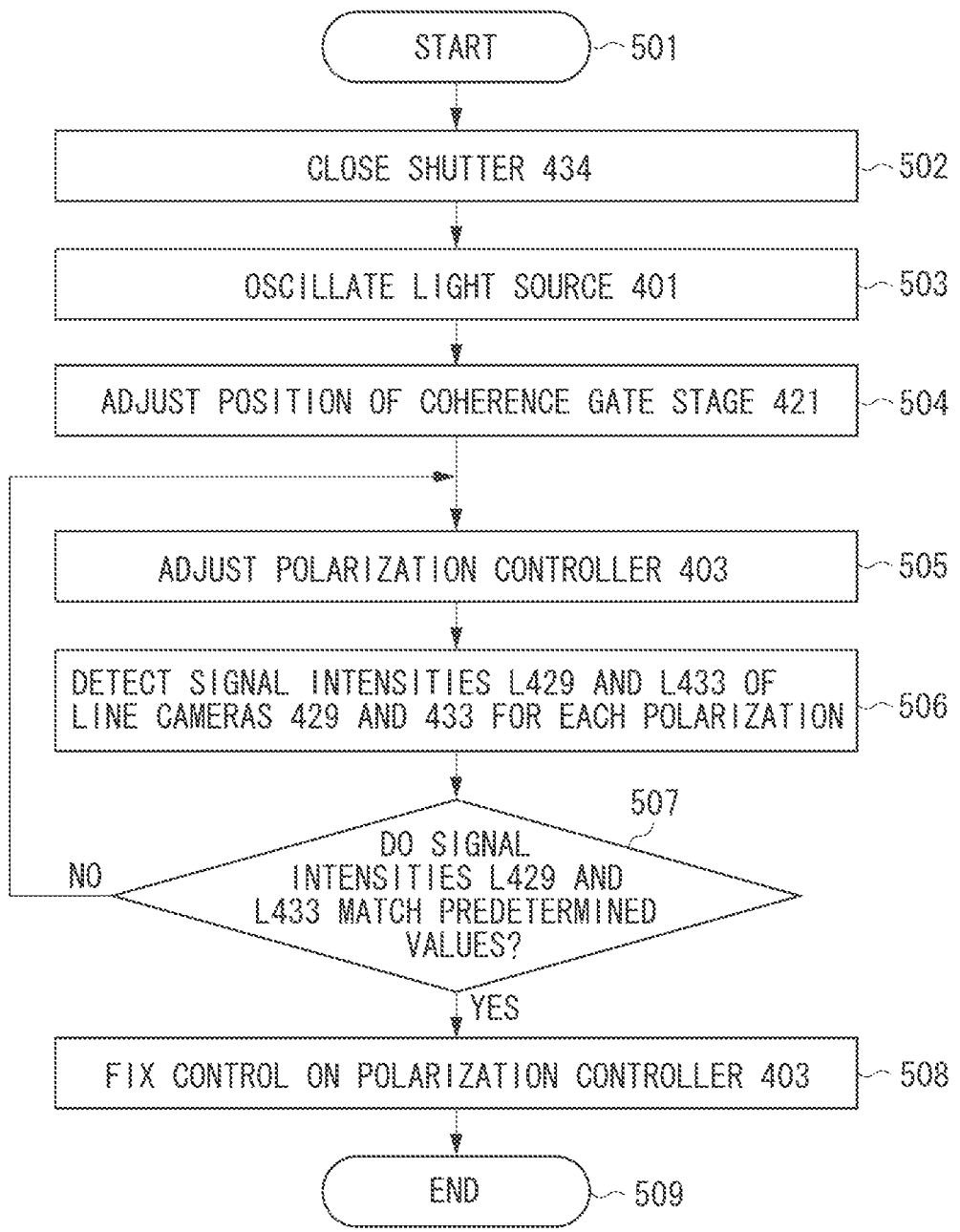

CONTROL APPARATUS AND CONTROL METHOD

CROSS-REFERENCE TO RELATED APPLICATIONS

This application is a Continuation of co-pending U.S. patent application Ser. No. 13/742,987, filed Jan. 16, 2013, which claims foreign priority benefit of Japanese Patent Application No. 2012-010276 filed Jan. 20, 2012. The above-named applications are hereby incorporated by reference herein in their entirety.

BACKGROUND OF THE INVENTION

Field of the Invention

The present invention relates to a control apparatus and a control method.

Description of the Related Art

In recent years, optical coherence tomography OCT) and a scanning laser opthalmoscope (SLO) are being developed in the field of ophthalmologic apparatuses for imaging optical characteristics and movement of a fundus tissue of the eye.

A polarization-sensitive OCT and a polarization-sensitive SLO, which are examples of the OCT and the SLO, perform imaging using polarization parameters (i.e., retardation and orientation) that are optical characteristics of the fundus tissue.

For example, the polarization-sensitive OCT uses the polarization parameter to generate a polarization-sensitive OCT image and distinguish and perform segmentation of the fundus tissue. International Publication No. WO 2010/122118 A1 discusses employing a light beam that has been modulated to a circularly-polarized beam as a measuring beam for examining the sample. Detection is then performed by splitting the interference beam into two linearly-polarized beams perpendicular to each other, so that the polarization-sensitive OCT image is generated.

However, the apparatus discussed in International Publication No. WO 2010/122118 A1 cannot perform calibration in the case where a polarization state changes along with usage of the apparatus.

SUMMARY OF THE INVENTION

The present invention is directed to an apparatus and a method capable of performing calibration of the polarization state. Such operational advantage is derived by each of configurations illustrated in exemplary embodiments of the present invention to be described below, and operational advantages that are not acquirable by conventional techniques are also included in the present invention.

According to an aspect of the present invention, a control apparatus includes an irradiation unit configured to irradiate a measurement object with a measuring beam, a restriction unit configured to restrict the measuring beam from being incident on the measurement object and to reflect or scatter the measuring beam, and a polarization control unit configured to control, based on the measuring beam reflected or scattered by the restriction unit, polarization of the measuring beam.

According to an exemplary embodiment of the present invention, the polarization state can be calibrated.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 2 is a flowchart illustrating a process performed according to the first exemplary embodiment.

FIG. 6 is a flowchart illustrating a process performed according to the second exemplary embodiment.

DESCRIPTION OF THE EMBODIMENTS

Various exemplary embodiments, features, and aspects of the invention will be described in detail below with reference to the drawings.

According to an exemplary embodiment of the present invention, an imaging apparatus is applicable to a subject such as an eye, the skin, and internal organs. Further, the imaging apparatus according to an exemplary embodiment of the present invention includes an ophthalmologic apparatus and an endoscope.

Figure 1:
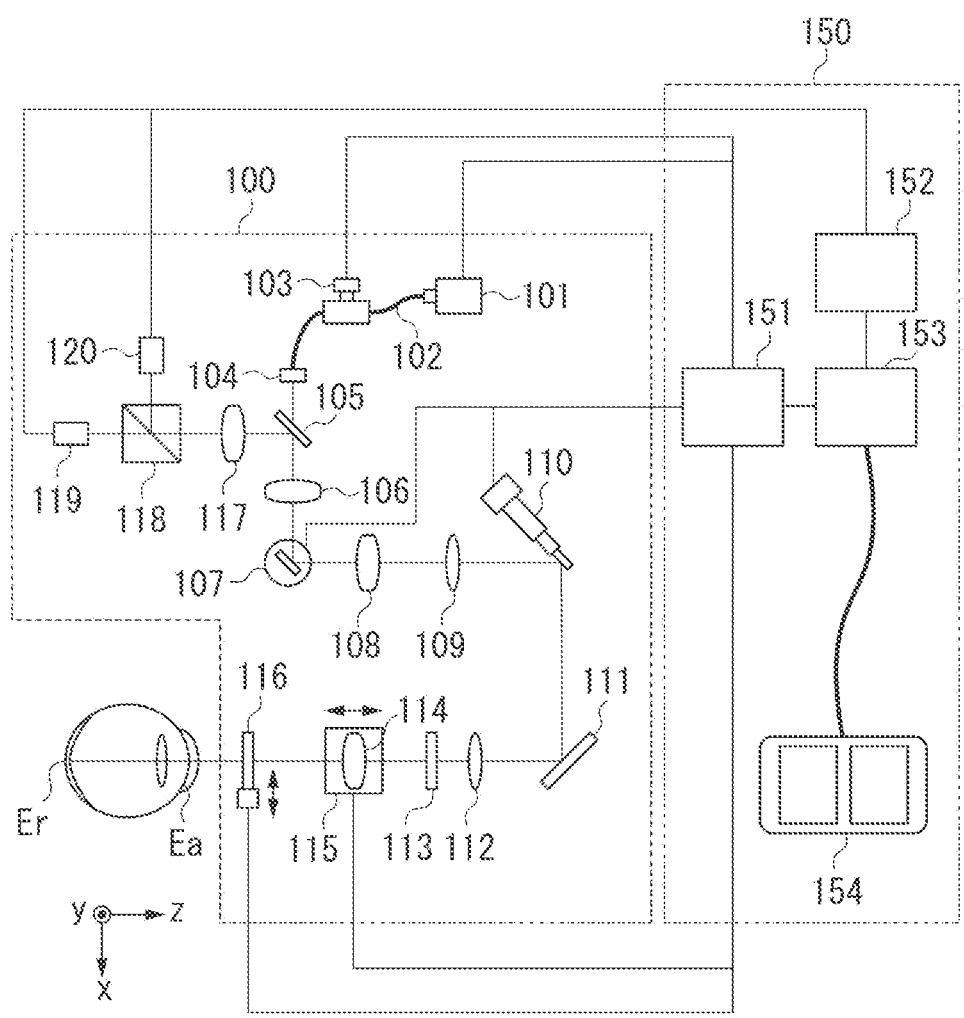
FIG. 1 is a schematic diagram illustrating a configuration of a control apparatus according to a first exemplary embodiment of the present invention.

FIG. 1 is an example of a schematic diagram illustrating the control apparatus according to the first exemplary embodiment of the present invention. Referring to FIG. 1, the control apparatus includes a polarization-sensitive SLO (hereinafter referred to as PS-SLO) 100 that employs polarization, and a polarization control apparatus 150.

Alight source 101, i.e., a semiconductor laser, emits light having a central wavelength of 780 nm. The measuring beam (i.e., an SLO measuring beam) emitted from the light source 101 is guided by a single mode (SM) fiber 102 to a polarization controller 103, which performs polarization control so that the measuring beam becomes a linearly-polarized beam. The linearly-polarized beam is then output from a collimator 104 as a parallel beam. The output measuring beam passes through a perforated portion of a perforated mirror 105 and a lens 106, and reaches a mirror 111 via an X scanner 107, lenses 108 and 109, and a Y scanner 110. The X scanner 107 includes a galvano mirror that scans the measuring beam in a horizontal direction on a fundus Er, and the Y scanner 110 includes a galvano mirror that scans the measuring beam in a vertical direction on the fundus Er.

The X scanner 107 and the Y scanner 110 are controlled by a drive control unit 151, and are capable of scanning the measuring beam in a desired range on the fundus Er. In other words, the X scanner 107 and the Y scanner 110 correspond to an example of mirrors that scan the measurement object with the measuring beam of which polarization has been controlled by a polarization controller. The measuring beam reflected off the mirror 111 passes through, via a lens 112, a λ/4 polarizing plate 113 arranged to be inclined at an angle of 45° from a P-polarization to an S-polarization direction with respect to a polarizing beam splitting surface of a polarizing beam splitter 118. The phase of the measuring beam is thus shifted by 90°, and the measuring beam is polarized to a circularly-polarized beam. The angle of the λ/4 polarizing plate 113 is not limited thereto. A focus lens 114 mounted on a stage 115 then focuses, via an anterior segment Ea of the subject's eye, the circularly-polarized measuring beam on retinal layers in the fundus Er. In other words, the light source 101 corresponds to an example of the irradiation unit that irradiates the measurement object with the measuring beam. Further, an optical system from the light source 101 to a unit just before the subject's eye corresponds to an example of an irradiation optical system.

According to the present exemplary embodiment, a shutter 116 is disposed to block the measuring beam before entering the subject's eye E. The shutter 116 is thus capable of preventing the measuring beam from being incident on the subject's eye. A drive control unit 151 controls the shutter 116, and the shutter 116 is closed when the fundus is not being measured. A mirror or a scattering body is attached to the other side of the shutter 116 with respect to the subject's eye E. In other words, the shutter 116 has a reflecting member such as a mirror on the side the measuring beam enters the subject's eye. The reflecting member is not limited to the mirror and may be any member capable of reflecting the measuring beam being incident on the measurement subject. As a result, the shutter 116 corresponds to an example of a restriction unit that restricts the measuring beam from being incident on the measurement object and reflects or scatters the measuring beam. Further, the shutter 116 corresponds to an example of a member that restricts the measuring beam scanned by a mirror from being incident on the measurement object and reflects or scans the measuring beam scanned by the mirror.

The measuring beam irradiating the fundus Er is reflected and scattered by each retinal layer, and reaches the perforated mirror 105 via the above-described optical path. The beam reflected by the perforated mirror 105 then passes through a mirror 117 and is split by the polarizing beam splitter 118 to beams of different polarization directions (i.e., a P-polarized beam and an S-polarized beam according to the present exemplary embodiment). The polarizing beam splitter 118 corresponds to an example of a splitting unit that splits, to beams of different polarizations, a returned beam obtained by irradiating the measurement object with the measuring beam.

The split beams are received by respective avalanche photodiodes (APD) 119 and 120, converted into electrical signals, and received by a signal processing unit 152. The APD 119 and 120 correspond to an example of a plurality of photodiodes that respectively receive the beams of different polarizations obtained by the polarizing beam splitter. According to the present exemplary embodiment, the APD 119 receives the P-polarized beam, and the APD 120 receives the S-polarized beam.

The electrical signals processed by the signal processing unit 152 are formed into images by a control unit 153 and displayed on a display device 154. The perforated mirror 105 is conjugate with the position of the pupil in the subject's eye, and reflects the light that has passed through a peripheral region of the pupil among the light reflected and scattered by the fundus Er irradiated with the measuring beam.

According to the present exemplary embodiment, the SM fiber is used. However, a similar configuration and effect may be acquired by using a polarization maintaining (PM) fiber and controlling polarization. Further, the SM fiber and the PM fiber can both be used. For example, the light source 101 and the polarization controller 103 may be connected by the SM fiber, and the polarization controller 103 and the collimator 104 may be connected by the PM fiber.

Furthermore, the control apparatus becomes capable of using only the beams in which the polarization directions are proximately the same by employing a polarizer. Moreover, the control apparatus may use a super luminescent diode (SLD) as the light source 101 to reduce speckles.

The polarization control apparatus 150 will be described below. The polarization control apparatus 150 includes the drive control unit 151, the signal processing unit 152, the control unit 153, and the display unit 154.

The drive control unit 151 controls each unit as described above. For example, the drive control unit 151 inserts and removes the shutter 116 with respect to the optical path connecting the subject's eye and the light source 101. If the shutter 116 is inserted in the optical path connecting the subject's eye and the light source 101, the drive control unit 151 performs control as follows. The drive control unit 151 causes the polarization controller 103 to control, based on the outputs from the APD 119 and 120, polarization of the measuring beam output from the light source 101. In other words, the drive control unit 151 corresponds to an example of a first control unit that inserts and removes a member with respect to the irradiation optical system. Further, if the first control unit has inserted the member in the irradiation optical system, the drive control unit 151 corresponds to an example of a second control unit that causes the polarization controller to control the polarization of the measuring beam based on the output from at least one of the plurality of photodiodes.

The signal processing unit 152 generates the images of the subject's eye based on the signals output from the APD 119 and 120, analyzes the generated images, and generates visualization information of the analysis results. The signal processing unit 152 may also only generate the images of the subject's eye based on the signals output from the APD 119 and 120. In such a case, the signal processing unit 152 corresponds to an example of an image acquisition unit that acquires, based on at least one of the beams of different polarizations obtained by splitting the returned beam acquired by irradiating the measurement object with the measuring beam, an image of the measurement object. Further, if the first control unit has removed the member from the irradiation optical system, the signal processing unit 152 corresponds to an example of an image acquisition unit that acquires the image of the measurement object based on an output from at least one of a plurality of photodiodes.

The control unit 153 controls the entire apparatus and also displays on a display screen of the display unit 154 the images generated by the signal processing unit 152. The control unit 153 in an adjustment mode to be described below causes the drive control unit 151 to control the polarization controller 103. Further, the control unit 153 causes the drive control unit 151 to control the polarization controller 103 based on detected intensities of the signals output from the APD 119 and 120. In other words, the drive control unit 151 corresponds to an example of a polarization control unit that controls the polarization of the measuring beam based on the light reflected or scattered by the restriction unit. The drive control unit 151 may control the polarization of the measuring beam based on the reflected light and the scattered light. Furthermore, the polarization controller 103 controls the polarization of light output from the light source under control of the drive control unit 151.

Moreover, the control unit 153 causes the drive control unit 151 to insert and remove the shutter 116 with respect to the optical path. In other words, the shutter 116 can be inserted in or removed from the optical path connecting the measurement object and the irradiation unit.

The display unit 154 displays various types of information under control of the control unit 153.

The image data generated by the signal processing unit 152 may be transmitted to the control unit 153 by wired or wireless communication. The display unit 154 displays display forms indicating the various types of information under control of the control unit 153, and the control unit 153 may transmit the image data to the display unit 154 by wired or wireless communication. Further, according to the present exemplary embodiment, the display unit 154 is included in the polarization control apparatus 150. However, the present invention is not limited thereto, and the display unit 154 may be separated from the polarization control apparatus 150. Furthermore, a portable device (i.e., a tablet) configured by integrating the control unit 153 and the display unit 154 may be used. In such a case, it is desirable to include a touch panel function in the display unit, so that a user can operate the touch panel to move the display position of the images, enlarge and reduce the images, and change the images to be displayed.

Image generation and image analysis processes performed in the signal processing unit 152 will be described below.

The signal processing unit 152 aligns the signals output from the APD 119 and 120 in synchronization with driving of the X scanner 107 and the Y scanner 110. The signal processing unit 152 thus generates two fundus images based on respective polarization components (i.e., a fundus image corresponding to the first polarized beam and a fundus image corresponding to the second polarized beam). Further, the signal processing unit 152 generates a fundus intensity image from the two fundus images (i.e., planar images). The pixel value r of the intensity image is calculated from signals $A_H$ and $A_V$ acquired from each of the APD 119 and 120 using equation (1). The signal processing unit 152 may generate an image of the subject's eye based on the signal output from APD 119 or APD 120.

$$r = \sqrt{A_H^2 + A_V^2} \quad (1)$$

The PS-SLO performs calibration in the adjustment mode before performing measurement, for acquiring a stable image. FIG. 2 is a flowchart illustrating an example of a calibration method. The adjustment mode corresponds to an example of a first mode in which the polarization control unit controls the polarization of the measuring beam.

In step 201, an operator presses a calibration start button (not illustrated) displayed on the display unit 154 or physically disposed on the apparatus, so that the adjustment mode is selected and the apparatus starts the calibration. In step 202, the drive control unit 151 closes the shutter 116. In step 203, the drive control unit 151 oscillates the light source 101. When the shutter 116 is closed, the light from the light source 101 via each of the lenses and mirrors is reflected or scattered by the mirror or the scattering body disposed on the shutter 116. The reflected or scattered light then returns to the perforated mirror 105. The light reflected by the perforated mirror 105 via the lens 117 is split by the polarizing beam splitter 118 into beams of different polarizations (i.e., the P-polarized beam and an S-polarized beam according to the present exemplary embodiment), similarly as the beam from the fundus. In other words, the polarizing beam splitter 118, which corresponds to an example of a splitting unit, splits the measuring beam reflected or scattered by the restriction unit into beams of different polarizations. Further, the polarizing beam splitter 118 splits, into beams of different polarizations, the measuring beam reflected or scattered by the member, or the return beam from the measurement object.

The split beams are respectively received by the APD 119 and 120, converted into electrical signals, and processed by the signal processing unit 152. In step 204, the drive control unit 151 adjusts the polarization controller 103. In step 205, the signal processing unit 152 detects the values of the signal intensities output from the APD 119 and 120. In step 206, the signal processing unit 152 determines whether signal intensity values I119 and I120 output from the APD 119 and 120 have reached the desired values. An example of the desired value is an initial signal intensity value obtained when there is no shift in polarization that is caused by heat generated along with usage of the apparatus.

If the signal processing unit 152 determines that the signal intensity values I119 and I120 have not reached the desired values (NO in step 206), the processes of step 204 and step 205 are repeated until the signal intensity values I119 and I120 have reached the desired values. If the signal processing unit 152 determines that the signal intensity values I119 and I120 have reached the desired values (YES in step 206), the process proceeds to step 207. In step 207, the drive control unit 151 fixes control on the polarization controller 103. In step 208, polarization adjustment ends. For example, the signal processing unit 152 determines whether the signal intensity value I119 is greater than or equal to a predetermined threshold value. If the signal intensity value I119 is greater than or equal to the predetermined threshold value, the adjustment process ends. The signal processing unit 152 may instead determine whether the signal intensity value I120 is greater than or equal to a predetermined threshold value. If the signal intensity value I120 is greater than or equal to the predetermined threshold value, the adjustment process ends. Further, the adjustment process may be ended in the case where the signal intensity value I119 is greater than or equal to a first threshold value and the signal intensity value I120 is smaller than or equal to a second threshold value that is smaller than the first threshold value. In other words, the drive control unit 151, which corresponds to an example of the polarization control unit, controls the polarization of the measuring beam based on at least one of the beams of different polarizations obtained by splitting the measuring beam reflected or scattered by the restriction unit.

The calibration method is not limited to the above-described method, and may be performed as follows. In step 204, the drive control unit 151 controls the polarization controller 103, and changes the polarization of the measuring beam over the entire range controllable by the polarization controller 103. The signal processing unit 152 then detects the signal intensity values I119 and I120 for each polarization of the measuring beam.

The drive control unit 151 thus performs calibration by controlling, based on the detection result, the polarization controller 103 to be in a state in which the value of the signal intensity value I119 becomes maximum, or in which the value of the signal intensity value I120 becomes minimum. The drive control unit 151 may control the polarization controller 103 to be in a state in which the value of the signal intensity value I119 becomes maximum and the value of the signal intensity value I120 becomes minimum. Further, if there is no case where the value of the signal intensity value I119 becomes maximum and the value of the signal intensity value I120 becomes minimum according to the detected result, the drive control unit 151 may control the polarization controller 103 as follows. The drive control unit 151 may control the polarization controller 103 to be in a state in which the value of the signal intensity value I119 becomes maximum or the value of the signal intensity value I120 becomes minimum. By controlling the polarization as described above, the polarization can be caused to be in a desired state.

The control information used by the drive control unit 151 with respect to the polarization controller 103 is stored in a memory (not illustrated) in association with the signal intensity values I119 and I120. As a result, by reading the control information from the memory, the drive control unit 151 can control the polarization controller 103 to the state of the polarization controller 103 in which the signal intensity value I119 becomes maximum and/or the signal intensity value I120 becomes minimum.

According to the above-described example, the polarization of the measuring beam is changed over the entire range that is controllable by the polarization controller 103. However, it is not limited thereto, and the range of the polarization to be changed by the polarization controller 103 may be an arbitrary range. For example, if it is known from past measurements that the maximum value of the signal intensity value I119 or the minimum value of the signal intensity value I120 appears in a predetermined range that is narrower than the entire range controllable by the polarization controller 103, the range of polarization to be changed by the polarization controller 103 may be the predetermined polarization range.

As described above, calibration can be promptly performed by restricting the range of polarization to be changed by the polarization controller 103. Further, if the polarization is controlled by applying on the fiber an external force such as a pressing force, the external force applied to the fiber can be reduced by restricting the range of polarization to be changed by the polarization controller 103. Failures such as breakage of the fiber can thus be prevented. Furthermore, since failures such as the breakage of the fiber can be prevented, longevity of the apparatus can be enhanced.

According to the present exemplary embodiment, the λ/4 polarizing plate 113 is arranged to be inclined at an angle of 45° as described above. In such a case, a vertical linearly-polarized beam which passes through the λ/4 polarizing plate 113 becomes a circularly-polarized beam. The circularly-polarized beam which is then reflected by the shutter 116 and again passes through the λ/4 polarizing plate 113 becomes a horizontal linearly-polarized beam. As a result, the intensity of one polarized beam among the beams obtained by splitting via the polarizing beam splitter 118 becomes large, and the intensity of the other polarization beam becomes small. If the beam entering the λ/4 polarizing plate 113 is a completely vertical linearly-polarized beam, the intensity of the polarization beam in the horizontal direction is maximized, and the intensity of the polarization beam in the vertical direction becomes minimized (e.g., proximately 0). In other words, the polarization controller 103 is adjusted so that the intensity of the polarization beam in the vertical direction among the signal intensity values I119 and I120 becomes minimized (e.g., proximately 0). Further, if the maximum intensity is previously known, the polarization controller 103 is adjusted so that the intensity of the polarization beam in the horizontal direction among the signal intensity values I119 and I120 becomes the previously known maximum intensity. Furthermore, both of the above-described control may be combined.

According to the above-described example, the vertically-polarized beam enters the λ/4 polarizing plate 113. However, it is not limited thereto. For example, if the horizontal linearly-polarized beam enters the λ/4 polarizing plate 113, the beam is reflected by the shutter 116 and again passes through the λ/4 polarizing plate 113, so that the beam becomes a vertical linearly-polarized beam. If the beam entering the λ/4 polarizing plate 113 is a completely horizontal linearly-polarized beam, the intensity of the polarized beam in the vertical direction becomes maximum, and the intensity in the horizontal direction becomes minimum (e.g., proximately 0). The polarization controller 103 thus becomes capable of performing adjustment, similarly as in the case where the beam entering the λ/4 polarizing plate 113 is the vertically-polarized beam.

Further, if the λ/4 polarizing plate 113 is inclined at 22.5°, the beam which has passed through the λ/4 polarizing plate 113 becomes an elliptically-polarized beam. If the elliptically-polarized beam is then reflected by the shutter 116 and again passes through the λ/4 polarizing plate 113, the beam becomes a linearly-polarized beam inclined at 45°. As a result, if the beam entering the λ/4 polarizing plate 113 is a completely vertical linearly-polarized beam, the intensities of the respective polarized beams obtained by the polarizing beam splitter 118 splitting the beam become the same. In other words, the polarization controller 103 is adjusted so that the signal intensity values I119 and I120 become the same. The process is similar for the case where the beam entering the λ/4 polarizing plate 113 is the horizontally-polarized beam.

More specifically, the control unit 153 changes the calibration method according to the inclination of the λ/4 polarizing plate 113. For example, the control unit 153 acquires the angle of the λ/4 polarizing plate 113, and changes the calibration method based on the acquired angle of the λ/4 polarizing plate 113.

Figure 3A:
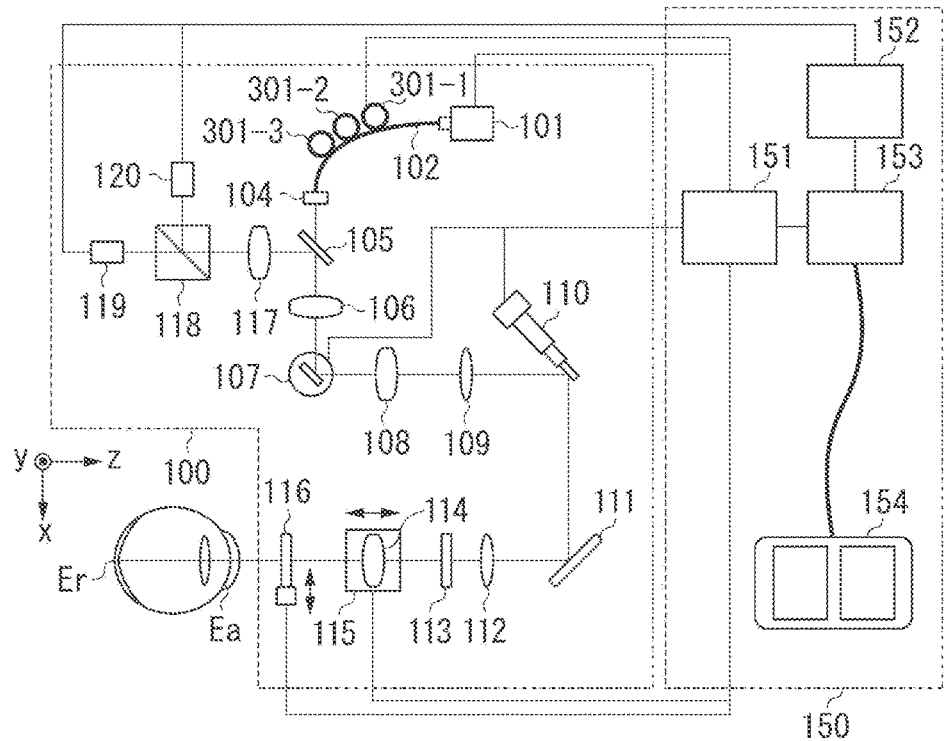
FIGS. 3A and 3B illustrate application examples according to the first exemplary embodiment.
Figure 3B:
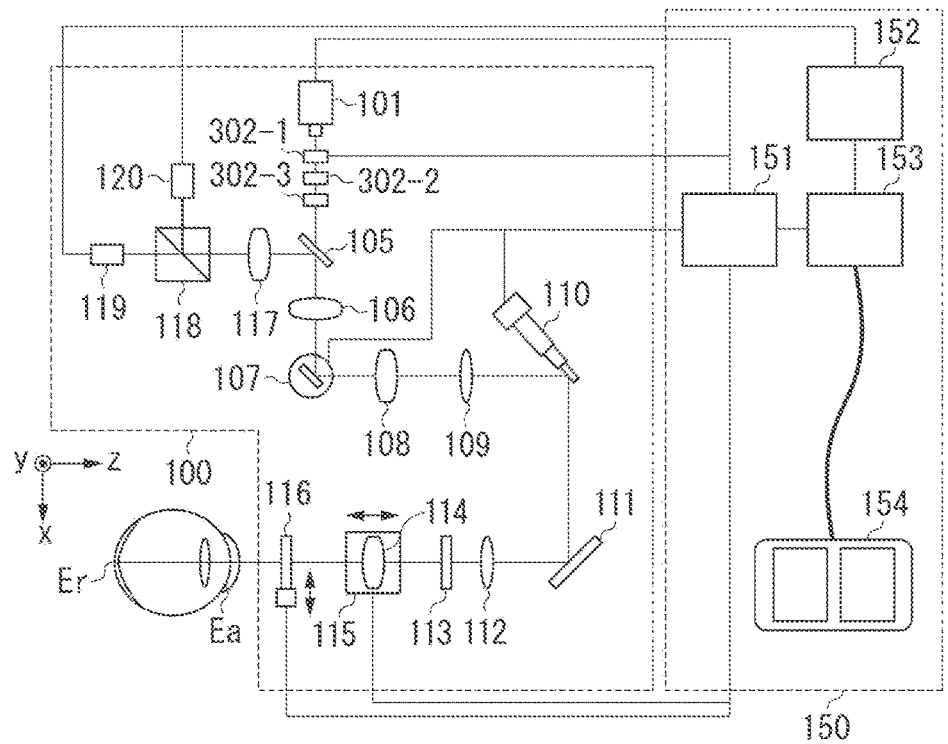

According to the present exemplary embodiment, an in-line polarization controller is used as the polarization controller for performing calibration. However, it is not limited thereto. For example, referring to FIG. 3A, paddle-shaped polarization controllers 301-1, 301-2, and 301-3 having a plurality of paddles may be used to control polarization. Further, referring to FIG. 3B, a polarization controller employing λ/4 polarizing plates 302-1 and 302-3 and a λ/2 polarizing plate 302-2 may be used to control polarization.

After the control unit 153 completes the calibration in the adjustment mode, an image capturing mode is automatically selected, and the drive control unit 151 removes the shutter 116 from the optical path, so that normal image capturing can be performed. Since the apparatus automatically shifts from the adjustment mode to the image capturing mode after completing the calibration, the apparatus can promptly shift to an image capturing operation after completing calibration. The image capturing mode corresponds to an example of a second mode in which the image of the measurement object is acquired. Further, the drive control unit 151 corresponds to a control unit which inserts, when the mode is in the first mode, the restriction unit in the optical path, and removes, when the mode is in the second mode, the restriction unit from the optical path.

The shutter 116 may be disposed between the perforated portion of the perforated mirror 105 and the lens 106, in which the beam is a parallel beam. The shutter 116 thus becomes capable of more efficiently reflecting the beam, and the calibration can be accurately performed even when the light amount entering the shutter 116 is small. Since the calibration can be performed even when the light amount is small, the calibration can also be performed before the light output from the light source 101 becomes a steady state. The calibration can thus be performed immediately after activating the apparatus, so that accurate measurement can be promptly performed.

Further, the shutter 116 may be disposed in front or behind the Y scanner 110, which is conjugate with the fundus and is the position at which the beam converges, to further reduce the size of the shutter 116. In such a case, the reflective intensity of the beam may become small, so that a reflecting member may be convex-shaped or concave-shaped. If the shutter 116 is disposed in front of the Y scanner 110 (i.e., between the lens 109 and the Y scanner 110), since the light passing through the lens 109 travels towards an optical axis, the light converges with respect to the shutter 116. As a result, the light reflected by the shutter 116 more easily passes through the lens 109, and the light amount received by the APD is prevented from decreasing as compared to when disposing the shutter 116 behind the Y scanner 110. The calibration can thus be accurately performed.

If the reflective intensity of light of the reflecting member of the shutter 116 is small, the reflective member is formed into a concave shape to increase the reflective intensity. If the reflective intensity is excessively large, the reflective member is formed into a convex shape to decrease the reflective intensity. There may be both the convex-shaped reflecting member and the concave-shaped reflecting member, so that the control unit 153 determines the reflecting member to be inserted in the optical path based on the output from the APD. For example, if the output from the APD is low, the control unit 153 inserts the concave-shaped reflecting member in the optical path, and if the output from the APD is excessively high, the control unit 153 inserts the convex-shaped reflecting member in the optical path.

As described above, according to the present exemplary embodiment, the shutter having a reflecting surface (i.e., a mirror) is arranged in the vicinity of the subject's eye and used when performing adjustment, so that adjustment can be performed in a state similar to when capturing an image. As a result, stable image capturing can be performed. Further, according to the present exemplary embodiment, the polarization state can be calibrated even when the polarization state of the measuring beam has changed due to heat generated by using the apparatus, so that a stable image can be obtained.

Figure 4:
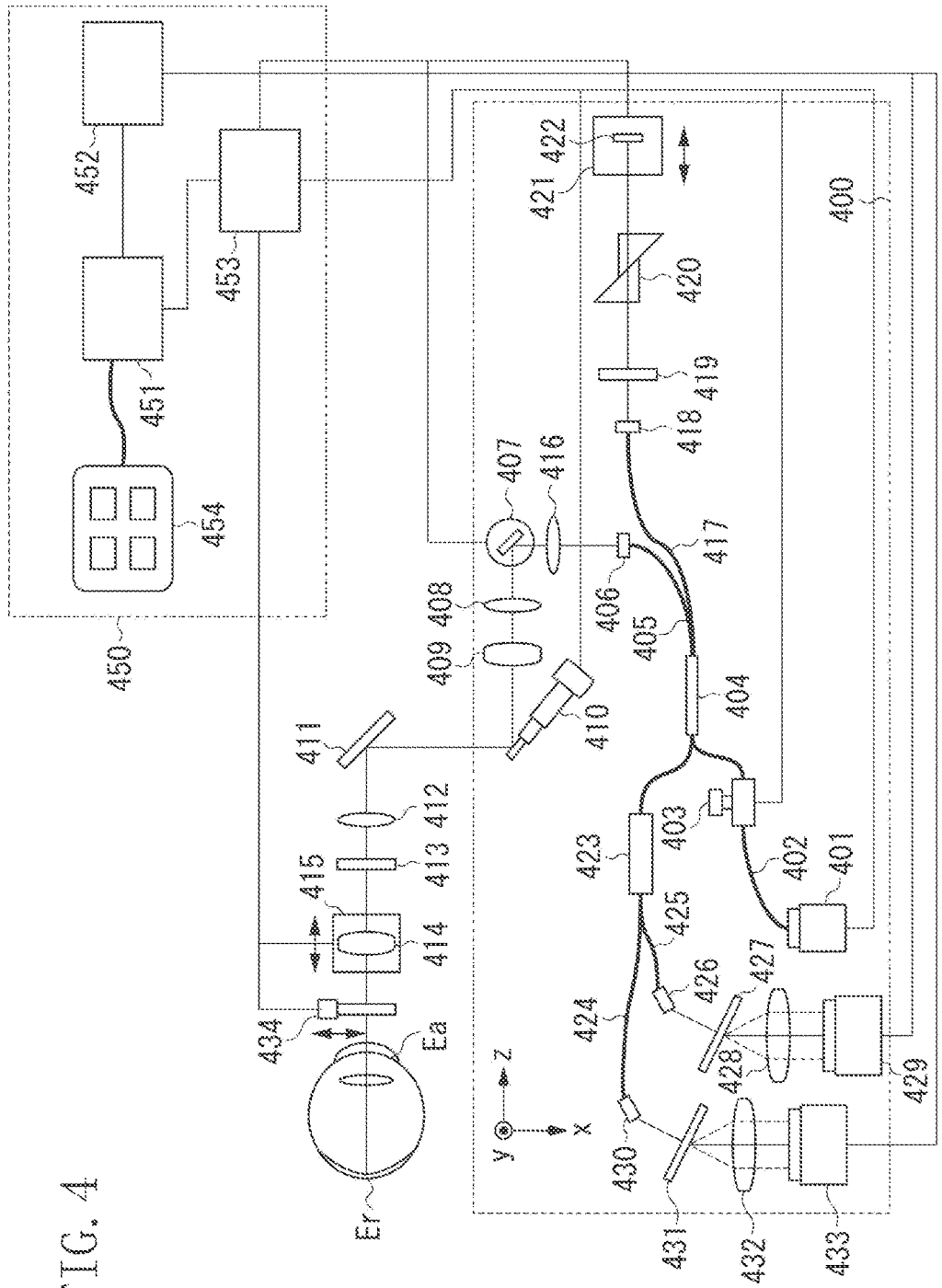
FIG. 4 is a schematic diagram illustrating a configuration of a control apparatus according to a second exemplary embodiment of the present invention.

FIG. 4 is a schematic diagram illustrating a configuration of an ophthalmologic apparatus according to a second exemplary embodiment of the present invention. Referring to FIG. 4, the ophthalmologic apparatus includes a polarization-sensitive OCT (PS-OCT) 400 and a polarization control apparatus 450.

The PS-OCT 400 will be described below. A light source 401 made of a super luminescent diode (SLD), i.e., a low-coherent light source, emits light having a central wavelength of 850 nm and a bandwidth of 50 nm. Any light source that can emit low coherent light, such as an amplified spontaneous emission (ASE) light source, may be used as the light source 401.

The light emitted from the light source 401 is guided by an SM fiber 402 and a polarization controller 403 to a fiber coupler 404 having a polarization preserving function. The beam is then split into the measuring beam (i.e., an OCT measuring beam) and a reference beam.

The polarization controller 403 adjusts the polarization state of the beam emitted from the light source 401, and adjusts the beam to a linearly-polarized beam. A branching ratio of the fiber coupler 404 is 90 (reference beam): 10 (measuring beam). The fiber coupler 404 corresponds to an example of a first coupler that splits into the measuring beam and the reference beam, the beam of which polarization has been controlled by the polarization controller. The measuring beam is output from a collimator 406 via a PM fiber 405 as a parallel beam.

The output measuring beam is converged by a lens 416. The beam which has passed through the lens 416 reaches a dichroic mirror 411 via an X scanner 407, lenses 408 and 409, and a Y scanner 410. The X scanner 407 includes a galvano mirror that scans the measuring beam in a horizontal direction on a fundus Er, and the Y scanner 410 includes a galvano mirror that scans the measuring beam in a vertical direction on the fundus Er.

The X scanner 407 and the Y scanner 410 are controlled by a drive control unit 453, and are capable of scanning the measuring beam in a desired range on the fundus Er. The X scanner 407 and the Y scanner 410 correspond to examples of the mirrors that scan the measuring beam with respect to the measurement object. The measuring beam reflected off the dichroic mirror 411 passes through, via a lens 412, a λ/4 polarizing plate 413. The beam passes through the λ/4 polarizing plate 413 arranged to be inclined at an angle of 45° from a P-polarization to the S-polarization direction with respect to the polarization splitting surface of the fiber coupler 423 including a polarizing beam splitter. The phase of the beam is then shifted by 90°, and is polarized to a circularly-polarized beam. The angle of the λ/4 polarizing plate 413 is not limited thereto.

A focus lens 414 mounted on a stage 415 focuses the circularly-polarized measuring beam on the retinal layers in the fundus Er via the anterior segment Ea of the subject's eye. The measuring beam irradiating the fundus Er is reflected and scattered by each retinal layer, and returns to the fiber coupler 404 via the above-described optical path. The optical system from the light source 401 to a unit just before the subject's eye corresponds to an example of the irradiation optical system. On the other hand, the reference beam obtained by splitting of the fiber coupler 404 is output via a PM fiber 417 from the collimator 418 as a parallel beam. A λ/4 polarizing plate 419 arranged to be inclined at 22.5° from the P-polarization direction to the S-polarization direction performs polarization control on the output reference beam, similarly as the measuring beam.

The reference beam is reflected via a dispersion compensation glass 420 by a mirror 422 mounted on a coherence gate stage 421, and returns to the fiber coupler 404. The reference beam passes through the λ/4 polarizing plate 419 twice, so that the linearly-polarized beam returns to the fiber coupler 404.

The coherence gate stage 421 is controlled by the drive control unit 453 to deal with differences in an axial length of the subject's eye. The measuring beam and the reference beam that have returned to the fiber coupler 404 are combined into an interference beam, which corresponds to an example of a first combined beam. The interference beam becomes incident on the fiber coupler 423 including a polarizing beam splitter.

The interference beam is then split by the fiber coupler 423 at the branching ratio of 50:50 into beams of different polarization directions (i.e., the P-polarized beam and the S-polarized beam according to the present exemplary embodiment). The fiber coupler 423 thus corresponds to an example of a splitting unit that splits into beams of different polarizations, the first combined beam obtained by combining the return beam obtained by irradiating the measurement object with the measuring beam, and the reference beam.

According to the present exemplary embodiment, a shutter 434 is arranged between the subject's eye E and the focus stage 415 to block the optical path, similarly as in the first exemplary embodiment. The drive control unit 453 controls the shutter 434, and the shutter 434 is closed when not measuring the fundus. A scattering body or a mirror is attached to the other side of the shutter 434 with respect to the subject's eye E. The shutter 434 thus has a scattering member on the side the measuring beam enters the subject's eye. In other words, the shutter 434 corresponds to an example of the restriction unit that restricts the measuring beam from being incident on the measurement object and reflects or scatters the measuring beam. Further, the shutter 434 is an example of the member that restricts the measuring beam scanned by the mirror from being incident on the measurement object and reflects or scans the measuring beam scanned by the mirror.

The P-polarized beam is dispersed by a grating 431 via a PM fiber 424 and a collimator 430, and is received by a lens 432 and a line camera 433. The S-polarized beam is similarly dispersed by a grating 427 via a PM fiber 425 and a collimator 426, and is received by a lens 428 and a line camera 429. The line cameras 429 and 433 correspond to an example of a plurality of line cameras that respectively receive the beams of different polarizations obtained by a second coupler.

The gratings 427 and 431 and the line cameras 429 and 433 are arranged to match the direction of each polarization direction. The beams received by the respective line cameras 429 and 433 are output as the electrical signals corresponding to the intensities of the beams. A signal processing unit 452 then receives the output electrical signals.

The inclinations of the λ/4 polarizing plates 413 and 419 which are adjusted based on the polarizing beam splitter may also be adjusted with respect to a line connecting centers of an optic disk and a macula in the fundus. Further, a similar result can be acquired by adjusting the polarizing beam splitter and the λ/4 polarizing plates 413 and 419 based on the vertical direction as a polarization basis.

The polarization control apparatus 450 will be described below. The polarization control apparatus 450 includes the drive control unit 453, the signal processing unit 452, a control unit 451, and a display unit 454.

The drive control unit 453 controls each unit as described above. For example, the drive control unit 453 inserts and removes the shutter 434 with respect to the optical path connecting the subject's eye and the light source 401. If the shutter 434 is inserted in the optical path connecting the subject's eye and the light source 401, the drive control unit 453 performs control as follows. The drive control unit 453 causes the polarization controller 403 to control, based on the output from the line cameras 429 and 433, polarization of the measuring beam output from the light source 401. In other words, the drive control unit 453 corresponds to an example of a first control unit that inserts and removes the member with respect to the irradiation optical system. Further, if the first control unit has inserted the member in the irradiation optical system, the drive control unit 453 corresponds to an example of a second control unit that causes the polarization controller to control the polarization of the measuring beam based on the output from at least one of the plurality of line cameras.

The signal processing unit 452 generates the images of the subject's eye based on the signals output from the line cameras 429 and 433, analyzes the generated images, and generates visualization information of the analysis results. The signal processing unit 452 may also only generate the images of the subject's eye based on the signals output from the line cameras 429 and 433. The signal processing unit 452 thus corresponds to an example of an image acquisition unit that acquires, based on at least one of the beams of different polarizations obtained by splitting the first combined beam, the image of the measurement object. Further, if the first control unit has removed the member from the irradiation optical system, the signal processing unit 452 corresponds to an example of the image acquisition unit that acquires the image of the measurement object based on an output from at least one of a plurality of line cameras.

The control unit 451 controls the entire apparatus and also displays on a display screen of the display unit 454 the images generated by the signal processing unit 452. The control unit 451 in the adjustment mode to be described below causes the drive control unit 453 to control the polarization controller 403. Further, the control unit 451 causes the drive control unit 453 to control the polarization controller 403 based on detected intensities of the signals output from the line cameras 429 and 433. In other words, the drive control unit 453 corresponds to an example of a polarization control unit that controls the polarization of the measuring beam based on the light reflected or scattered by the restriction unit. The drive control unit 453 may control the polarization of the measuring beam based on the reflected light and the scattered light. Further, the polarization control unit 453 corresponding to an example of a polarization control unit controls the polarization of the measuring beam based on at least one of the beams of different polarizations obtained by splitting a second combined beam. Furthermore, the polarization controller 403 controls the polarization of light output from the light source under control of the drive control unit 453. The second combined beam corresponds to the beam obtained by combining the measuring beam which has been reflected or scattered by the shutter 434 and the reference beam.

The display unit 454 displays various types of information under control of the control unit 451.

Image generation and image analysis processes performed in the signal processing unit 452 will be described below.

The signal processing unit 452 performs, on interference signals output from each of the line cameras 429 and 433, reconfiguration processing employed in a common spectral domain OCT (SD-OCT). The signal processing unit 452 thus generates two tomographic images based on the respective polarization components (i.e., the tomographic image corresponding to the first polarized beam and the tomographic image corresponding to the second polarized beam).

More specifically, the signal processing unit 452 performs fixed pattern noise cancellation on the interference signals. The fixed pattern noise cancellation is performed by averaging a plurality of A-scan signals that has been detected and thus extracting the fixed pattern noise, and subtracting the extracted fixed pattern noise from the input interference signal.

The signal processing unit 452 then transforms the wavelength of the interference signal to a wave number, and performs Fourier transform, so that a tomographic signal (i.e., a tomographic signal indicating the polarization state) is generated.

The signal processing unit 452 performs the above-described process for the interference signals of the two polarization components, and thus generates the two tomographic images.

Further, the signal processing unit 452 generates the tomographic intensity images from the above-described two tomographic signals.

More specifically, the tomographic intensity image is basically the same as the tomographic image in the conventional OCT. The pixel value r of the tomographic intensity image is calculated from the tomographic signals $A_H$ and $A_V$ acquired from each of the line cameras 429 and 433 using the above-described equation (1). FIG. 5A illustrates an example of the intensity image of the optic disk. The signal processing unit 452 may also generate an image of the subject's eye based on the signal output from the line camera 429 or 433.

Further, the signal processing unit 452 generates a retardation image from the tomographic images of the polarization components that are perpendicular to each other.

More specifically, a value δ of each pixel in the retardation image is a value indicating a ratio of the effects received by the vertical polarization component and the horizontal polarization component in the subject's eye, at the position of each pixel configuring the tomographic image. The value δ is calculated from each of the tomographic signals $A_H$ and $A_V$ using equation (2).

$$\delta = \arctan\left[\frac{A_V}{A_H}\right] \quad (2)$$

Figure 5B:
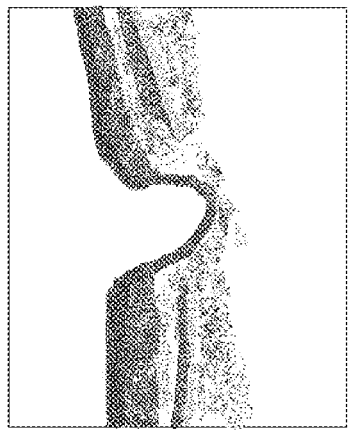
FIGS. 5A, 5B, 5C, 5D, and 5E illustrate examples of images generated by a signal processing unit.
Figure 5A:
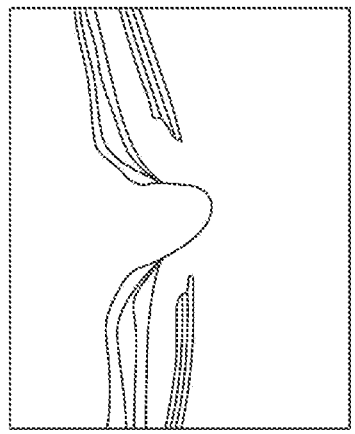

FIG. 5B illustrates an example of the retardation image of the optic disk generated as described above. The retardation image can be acquired by calculating equation (2) for each B-scan image. As described above, the retardation image is a tomographic image indicating the difference of the effect received by the two polarized beams in the subject's eye. Referring to FIG. 5B, the values indicating the above-described ratio are displayed as a color tomographic image. A darker-shaded portion indicates that the value of the ratio is small, and a lighter-shaded portion indicates that the value of the ratio is large. As a result, generating the retardation image enables recognizing a layer in which there is birefringence. For further details, refer to "E. Gotzinger et al., Opt. Express 13, 10217, 2005".

Furthermore, the signal processing unit 452 can similarly generate a retardation image in a planar direction of the fundus based on the outputs from the APD 152 and 153.

The signal processing unit 452 generates a retardation map from the retardation images acquired with respect to a plurality of B-scan images.

More specifically, the signal processing unit 452 detects a retinal pigment epithelium (RPE) in each B-scan image. Since the RPE cancels polarization, the signal processing unit 452 searches for a retardation distribution of each A-scan along the depth direction in the range from an inner limiting membrane (ILM) without including the RPE. The signal processing unit 452 then sets a maximum value of the retardation as a representative value of the retardation in the A-scan.

The signal processing unit 452 performs the above-described process on all retardation images, and thus generates the retardation map.

Figure 5E:
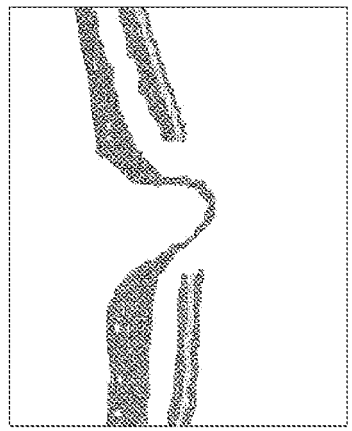
Figure 5D:
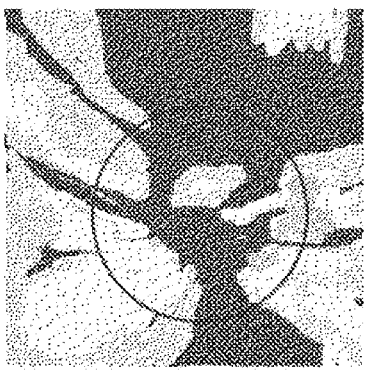
Figure 5C:
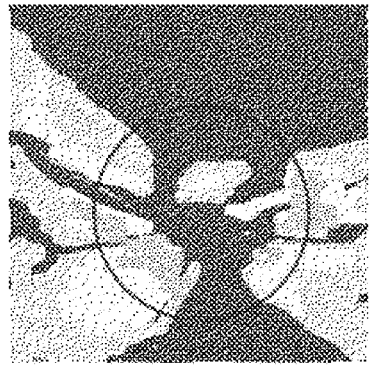

FIG. 5C illustrates an example of the retardation map of the optic disk. Referring to FIG. 5C, the darker-shaded portion indicates that the value of the ratio is small, and the lighter-shaded portion indicates that the value of the ratio is large. The layer having birefringence in the optic disk is a retinal nerve fiber layer (RNFL), and the retardation map illustrates the value indicating the ratio caused by the birefringence in the RNFL and the thickness of the RNFL. As a result, the value indicating the ratio becomes large where the RNFL is thick, and becomes small where the RNFL is thin. The thickness of the RNFL for the entire fundus thus becomes recognizable using the retardation map, and can be used in the diagnosis of glaucoma.

The signal processing unit 452 performs linear approximation of the value of the retardation δ in the range of ILM to RNFL in each A scan image of the previously generated retardation image. The signal processing unit 452 then determines the acquired slope as the birefringence at the position on the retina in the A-scan image. In other words, since retardation is a product of a distance and the birefringence in the RNFL, a linear relation is acquired by plotting the depth and the value of the retardation in each A-scan image. As a result, linear approximation is performed on the plot using a least square method, and the acquired slope becomes the value of the birefringence in the RNFL in the A-scan image. The signal processing unit 452 performs the above-described process on all of the acquired retardation images, and generates the map representing the birefringence.

FIG. 5D illustrates an example of the birefringence map of the optic disk. The birefringence map directly maps the values of the birefringence. As a result, when a fibrous architecture of the RNFL changes even if the thickness of the RNFL does not change, the change can be visualized as the change in the birefringence.

The signal processing unit 452 calculates a Stokes vector S for each pixel from the acquired tomographic signals $A_H$ and $A_V$, and a phase difference $\Delta\Phi$ between the tomographic signals $A_H$ and $A_V$, using equation (3).

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad (3)$$

In such a case, $\Delta\Phi$ is calculated from phases $\Phi_H$ and $\Phi_V$ of each signal acquired when calculating the two tomographic images, as $\Delta\Phi = \Phi_V - \Phi_H$.

The signal processing unit 452 then sets, in each B-scan image, a window of the size that is proximately 70 µm in a main scanning direction of the measuring beam and 18 µm in a depth direction. The signal processing unit 452 then averages each element of the Stokes vector calculated for each pixel by a number C within each window, and calculates a degree of polarization uniformity (DOPU) within the window using equation (4).

$$\text{DOPU} = \sqrt{Q_m^2 + U_m^2 + V_m^2} \quad (4)$$

In equation (4), $Q_m$, $U_m$, and $V_m$ are values acquired by averaging the elements Q, U, and V in the Stokes vector within each window. The signal processing unit 452 performs the above-described process for all windows in the B-scan images, and generates a DOPU image of the optic disk as illustrated in FIG. 5E. As described above, the DOPU image is a tomographic image indicating the degree of polarization uniformity of the two types of polarization.

DOPU is a value indicating the uniformity of polarization, and becomes close to "1" when polarization is preserved, and smaller than "1" when polarization is cancelled or not preserved. Since the RPE in the structure of the retina cancels the polarization state, the value of the DOPU in the portion corresponding to the RPE in the DOPU image becomes lower than the values in the other portions. Referring to FIG. 5E, the lighter-shaded portion indicates the RPE. The DOPU image visualizes the layer such as the RPE that cancels polarization, so that the image of the RPE can be accurately acquired as compared to the change in the intensity even when the RPE is deformed due to a disease.

According to the present exemplary embodiment, the above-described tomographic images corresponding to the first and second polarized beams, the retardation image, and the DOPU image will be referred to as tomographic images indicating the polarization state. Further, according to the present exemplary embodiment, the above-described retardation map and the birefringence map will also be referred to as fundus images indicating the polarization state.

The signal processing unit 452 uses the above-described intensity image to perform segmentation of the tomographic image.

More specifically, the signal processing unit 452 applies, to the tomographic image to be processed, a median filter as a type of smoothing filter, and a Sobel filter as a type of an edge detection method. The signal processing unit 452 thus generates respective images (hereinafter referred to as a median image and a Sobel image). The signal processing unit 452 then generates a profile for each A-scan from the generated median image and Sobel image. The signal processing unit 452 generates the profile of the intensity value from the median image and the profile of a gradient from the Sobel image. The signal processing unit 452 detects peaks in the profiles generated from the Sobel image. The signal processing unit 452 extracts a boundary of each retinal layer by referring to the profiles of the median image corresponding to regions before and after the detected peaks and the regions between the detected peaks.

Further, the signal processing unit 452 measures each layer thickness in the direction of the A-scan line, and generates a layer thickness map of each layer.

The PS-OCT uses the above-described apparatus and performs calibration in the adjustment mode before performing measurement as described below to acquire a stable image. The PS-OCT performs calibration according to the flowchart illustrated in FIG. 6 to be described below.

In step 501, the operator presses the calibration start button (not illustrated) displayed on the display unit 454 or physically disposed on the apparatus, so that the adjustment mode is selected and the apparatus starts the calibration. In step 502, the drive control unit 453 closes the shutter 434. In step 503, the drive control unit 453 oscillates the light source 401. The light which has been scattered by the scattering body attached to the back surface of the shutter 433 interferes in the fiber coupler 404. In other words, the fiber coupler 404 corresponds to an example of a second coupler that generates a combined beam obtained by combining the measuring beam that has been reflected or scattered by a member, or the return beam from the measurement object, and the reference beam. In step 504, the drive control unit 453 adjusts the position of the stage 421 so that an optical path length from the light source 401 to the shutter 434 becomes the same as the optical path length from the light source 401 to the mirror 422.

In step 505, the drive control unit 453 adjusts the polarization controller 403. In step 506, the signal processing unit 452 acquires, from the line cameras 429 and 433, respective signals L429 and L433. The signals L429 and L433 are changed by adjusting the polarization controller 403. According to the present exemplary embodiment, if the polarization controller 403 is rotated 45° clockwise towards an optical axis direction, the polarized beam from the polarization controller 403 changes to a circularly-polarized beam, and enters the back surface of the shutter 434 as a linearly-polarized beam. The light scattered by the back surface of the shutter 434 passes through the λ/4 polarizing plate 413 and becomes a circularly-polarized beam, returns to the fiber coupler 404, and interferes with the reference beam. The intensity values of the signals L429 and L433 thus become the same (in a strict sense, since the sensitivity of a sensor and the optical transmittance of each member are different, the intensity values do not necessarily match). The fiber coupler 423 then splits, into beams of different polarizations, the interference beam obtained by the fiber coupler 404. The fiber coupler 423 thus corresponds to an example of a splitting unit that splits the second combined beam obtained by combining the measuring beam reflected or scattered by the restriction unit and the reference beam. Further, the fiber coupler 423 corresponds to an example of a coupler that splits the combined beam into beams of different polarizations.

More specifically, an initial adjustment position of the polarization controller 403 in the apparatus (e.g., an ideal position) and the characteristics related to the signal intensity of the camera (i.e., at least one of the signal intensity and a graph shape of the signal intensity) are stored in advance. The graph represents the relation between the signal intensity and the position of the line camera, and the position on the line camera at which the peak of the signal intensity appears can be confirmed using the graph. In step 507, the signal processing unit 452 determines whether the signal intensity values of the respective signals L429 and L433 are the same as the stored signal intensity values. The signal processing unit 452 may determine that the values are the same in the case where the difference between the signal intensity values of the respective signals L429 and L433 and the stored signal intensity values are within a predetermined threshold value.

If the signal intensity values of the respective signals L429 and L433 are not the same as the stored signal intensity values (NO in step 507), the signal processing unit 452 repeats the processes of step 505 and step 506 until the values become the same. If the signal intensity values of the respective signals L429 and L433 are the same as the stored signal intensity values (YES in step 507), the process proceeds to step 508. In step 508, the drive control unit 453 fixes control on the polarization controller 403. In step 509, the drive control unit 453 ends adjustment of the polarization.

According to the above-described example, the polarization is adjusted using the signal intensity. However, the present invention is not limited thereto. For example, the signal processing unit 452 may perform determination based on only the graph shape. More specifically, the initial adjustment position of the polarization controller 403 in the apparatus and the graph shape as the characteristic of the signal intensity of the camera are stored in advance. The graph represents the relation between the signal intensity and the position of the line camera, and the position on the line camera at which the peak of the signal intensity appears can be confirmed using the graph.

The drive control unit 453 controls the polarization controller 403, and the signal processing unit 452 then detects the signal intensities of the signals L429 and L433 in the polarization states at that time. The signal processing unit 452 thus generates the above-described graph based on the detected signal intensities. The signal processing unit 452 then determines whether the graph shape matches the initial graph shape that has been stored. If the graph shapes match, or the difference in the graph shapes are within a predetermined threshold value, the drive control unit 453 fixes control on the polarization controller 403. On the other hand, if the graph shapes do not match, the drive control unit 453 re-performs control of the polarization states, and the signal processing unit 452 determines whether the graph shape matches the initial graph shape that has been stored. Since the signal intensity depends on the output from the light source (i.e., the light source output changes due to a power source and life), it is not necessary for the graphs to completely match. Further, the polarization may be adjusted based on the graph shape and the signal intensity.

Furthermore, the polarization may be adjusted by other methods. For example, the polarization controller 403 changes the polarization of the measuring beam over the entire range controllable thereby. The signal processing unit 452 then detects the signal intensities of the respective signals L429 and L433 in the respective polarizations.

The drive control unit 453 then uses the detection result and controls the polarization controller 403 to a state in which the intensity of the signal L429 or the signal L433 is approximately the same as the intensity in the ideal state. The drive control unit 453 thus performs calibration. The drive control unit 453 may also control the polarization controller 403 to a state in which the intensities of the signal L429 and the signal L433 are approximately the same as the intensities in the ideal state. Further, if the drive control unit 453 cannot recognize, from the detection results, the case where the intensities of the signal L429 and the signal L433 are approximately the same as the intensities in the ideal state, the drive control unit 453 may control the polarization controller 403 as follows. The drive control unit 453 may control the polarization controller 403 to be in a state in which the intensity of the signal L429 or the signal L433 is approximately the same as the intensity in the ideal state. By controlling the polarization as described above, the polarization can be controlled to be a desired state. The control information with respect to the polarization controller 403 used by the drive control unit 453 is stored in the memory (not illustrated) in association with the intensities of the signals L429 and L433. As a result, by reading the control information from the memory, the drive control unit 453 becomes capable of controlling the polarization controller 403 to be in a state in which the intensity of the signal L429 and/or the intensity of the signal L433 is approximately the same as the intensity in the ideal state.

According to the above-described exemplary embodiment, the polarization of the measuring beam is changed over the entire range controllable by the polarization controller 403. However, it is not limited thereto, and the range of polarization to be changed by the polarization controller 403 may be an arbitrary range. For example, if it is known from past measurements that the case where the intensity of the signal L429 or the signal L433 is approximately the same as the intensity in the ideal state appears in a predetermined range that is narrower than the entire range, the range of polarization to be changed by the polarization controller 403 may be set as the predetermined range of polarization.

As described above, calibration can be promptly performed by restricting the range of polarization to be changed by the polarization controller 403. Further, if the polarization is controlled by applying on the fiber an external force such as a pressing force, the external force applied to the fiber can be reduced by restricting the range of polarization to be changed by the polarization controller 403. Failures such as breakage of the fiber can thus be prevented. Furthermore, since failures such as the breakage of the fiber can be prevented, longevity of the apparatus can be enhanced.

Moreover, according to the above-described example, the detection unit for detecting both the signals L429 and L433 is used. However, a similar result can be acquired by detecting one of the signals.

Other calibration methods will be described below. A case where the λ/4 polarizing plate 413 is arranged to be inclined at an angle of 45° as described above will be considered. In such a case, a vertical linearly-polarized beam which passes through the λ/4 polarizing plate 413 becomes a circularly-polarized beam. The circularly-polarized beam which is then reflected by the shutter 434 and again passes through the λ/4 polarizing plate 413 becomes a horizontal linearly-polarized beam. As a result, the intensity of one polarized beam among the beams obtained by splitting by the fiber coupler 423 becomes large, and the intensity of the other polarization beam becomes small. If the beam entering the λ/4 polarizing plate 413 is a completely vertical linearly-polarized beam, the intensity of the polarized beam in the horizontal direction is maximized, and the intensity of the polarized beam in the vertical direction becomes minimized (e.g., proximately 0). In other words, the polarization controller 403 is adjusted so that the intensity of the polarized beam in the vertical direction among the intensities of the signals L429 and L433 becomes minimized (e.g., proximately 0). Further, if the maximum intensity is previously known, the polarization controller 403 is adjusted so that the intensity of the polarization beam in the horizontal direction among the intensities of the signals L429 and L433 becomes the previously known maximum intensity. Furthermore, both of the above-described control may be combined.

According to the above-described example, the vertically-polarized beam enters the λ/4 polarizing plate 413. However, it is not limited thereto. For example, if the horizontal linearly-polarized beam enters the λ/4 polarizing plate 413, the beam is reflected by the shutter 434 and again passes through the λ/4 polarizing plate 413, so that the beam becomes a vertical linearly-polarized beam. If the beam entering the λ/4 polarizing plate 413 is a completely horizontal linearly-polarized beam, the intensity of the polarized beam in the vertical direction becomes maximum, and the intensity in the horizontal direction becomes minimum (e.g., proximately 0). As a result, the polarization controller 403 becomes capable of performing adjustment, similarly as in the case where the beam entering the λ/4 polarizing plate 413 is the vertically-polarized beam.

Further, if the λ/4 polarizing plate 413 is inclined at an angle of 22.5°, the beam which has passed through the λ/4 polarizing plate 413 becomes an elliptically-polarized beam. If the elliptically-polarized beam is then reflected by the shutter 116 and again passes through the λ/4 polarizing plate 413, the beam becomes a vertical linearly-polarized beam inclined at 45°. As a result, if the beam entering the λ/4 polarizing plate 413 is a completely vertical linearly-polarized beam, the intensities of the respective polarized beams obtained by the fiber coupler 423 splitting the beam become the same. In other words, the polarization controller 403 is adjusted so that the values of the intensities of the signals L429 and L433 become the same. The process is similar for the case where the beam entering the λ/4 polarizing plate 413 is the horizontally-polarized beam.

More specifically, the calibration method is changed according to the inclination of the λ/4 polarizing plate 413. For example, the control unit 451 acquires the angle of the λ/4 polarizing plate 413, and changes the calibration method based on the angle of the λ/4 polarizing plate 413.

Further, if the polarization can be controlled, the polarization controller 403 may be another polarization controller similarly as in the first exemplary embodiment.

After completing calibration in the adjustment mode, the image capturing mode is automatically selected, and the drive control unit 453 removes the shutter 434 from the optical path, so that normal image capturing can be performed. Since the mode automatically shifts from the adjustment mode to the image capturing mode after completing calibration, the image capturing operation can be promptly performed after completing calibration.

Further, the shutter 434 may be disposed in front or behind the collimator 406, similarly as the shutter 116. Further, the shutter 434 may be disposed in front or behind the Y scanner 410, which is conjugate with the fundus, to further reduce the size thereof, similarly as the shutter 116. In such a case, since the light may become scattered and the reflective intensity of the beam may become small, the reflecting member may be convex-shaped or concave-shaped. Further, the control unit 451 may determine the reflecting member to be inserted in the optical path based on the reflective intensity of the APD, similarly as the shutter 116. For example, if the output from the APD is low, the control unit 451 inserts the concave-shaped reflecting member in the optical path, and if the output from the APD is excessively high, the control unit 451 inserts the convex-shaped reflecting member in the optical path.

As described above, according to the present exemplary embodiment, the shutter having a reflecting surface (i.e., a mirror) is disposed in the vicinity of the subject's eye, and the polarization is adjusted by adjusting the gate position. As a result, the adjustment can be performed in a similar state as when capturing an image, and image capturing can be stably performed.

According to the above-describe exemplary embodiments, the calibration is performed using the shutter 116. However, adjustment may be performed by the APD receiving the light reflected or scattered by a different member. Further, according to the above-described exemplary embodiment, calibration is started by the operator pressing the calibration start button. However, it is not limited thereto. For example, the calibration may be started by switching on/off the main body, or at every several hours (e.g., two hours) after switching the power on. The time intervals at which the calibration is performed may be changed by monitoring the temperature inside the apparatus, in view of the polarization state becoming changed due to the heat. For example, if the temperature inside the apparatus is a predetermined temperature or higher, the time interval of performing calibration is shortened. If the temperature inside the apparatus is lower than the predetermined temperature, the time interval is extended. By automatically performing the calibration as described above, a stable image can be obtained without an examiner being conscious of performing calibration. The polarization state may also be controlled based on the contrast of the acquired image.

Further, according to the above-described exemplary embodiments, the mirror or the scattering body is attached to the shutters 116 and 434. If the intensity of the light reflected by the mirror is too strong with respect to the sensor, a neutral density (ND) filter may be arranged in the optical path.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An imaging apparatus comprising:
    an irradiation unit configured to irradiate a measurement object with a measuring light;
    a reflection unit configured to reflect or scatter the measuring light;
    a polarization control unit configured to control, based on the measuring light reflected or scattered by the reflection unit, polarization of the measuring light;
    an image acquisition unit configured to acquire an image of the measurement object,
    wherein the reflection unit is configured to be placed in an optical path of the measuring light in a first mode which is a mode for controlling polarization of the measuring light by the polarization control unit, and the reflection unit is configured to be placed out of the optical path of the measuring light in a second mode which is a mode for acquiring the image.

2. The imaging apparatus according to claim 1, further comprising:
    a splitting unit configured to split, into lights of different polarizations, a return light obtained by irradiating the measurement object with the measuring light,
    wherein the image acquisition unit is configured to acquire the image based on at least one of the lights of different polarizations.

3. The imaging control apparatus according to claim 1, further comprising:
    a splitting unit configured to split, into lights of different polarizations, the measuring light reflected or scattered by the reflection unit,
    wherein the polarization control unit controls, based on at least one of the lights of different polarizations, polarization of the measuring light.

4. The imaging control apparatus according to claim 1, further comprising:
    a light source configured to emit light;
    a first splitting unit configured to split, into the measuring light and a reference light, the light emitted from the light source;

a combining unit configured to form a combined light by combining the reference light with a return light obtained by irradiating the measurement object with the measuring light; and a second splitting unit configured to split the combined light into lights of different polarizations;

wherein the image acquisition unit is configured to acquire the image based on at least one of the lights of different polarizations.

5. The imaging apparatus according to claim 1, further comprising:

a light source configured to emit light;

a first splitting unit configured to split, into the measuring light and a reference light, the light emitted from the light source;

a combining unit configured to form a combined light by combining the reference light with the measuring light reflected or scattered by the reflection unit; and a second splitting unit configured to split the combined light into lights of different polarizations, wherein the polarization control unit controls, based on at least one of the lights of different polarizations, polarization of the measuring light.

6. The imaging apparatus according to claim 1, wherein the measurement object is an eye.

7. The imaging apparatus according to claim 1, wherein the control by the polarization control unit is a calibration.

8. An imaging method comprising:

irradiating a measurement object with a measuring light;

providing a reflection unit that is configured to reflect or scatter the measuring light and that is further configured to be placed in and out of an optical path of the measurement light;

controlling, based on the light reflected or scattered by the reflection unit, polarization of the measuring light; and acquiring an image concerning the measurement object, wherein the reflection unit is placed in the optical path of the measurement light under a first mode in which polarization of the measuring light is controlled, and the reflection unit is placed out of the optical path of the measurement light under a second mode in which the image is acquired.

9. The imaging method according to claim 8, wherein the measurement object is an eye.

10. A non-transitory computer-readable storage medium storing a program that causes a computer to perform the imaging method according to claim 8.

11. An imaging apparatus comprising:

an irradiation optical system configured to irradiate a measurement object with a measuring light;

a polarization control unit configured to control, based on the measuring light reflected or scattered by a reflection unit that is configured to reflect or scatter the measurement light, polarization of the measuring light; and an image acquisition unit configured to acquire an image of the measurement object, wherein the reflection unit is configured to be placed in an optical path of the measuring light when the polarization control unit controls polarization of the measuring light, and the reflection unit is configured to be placed out of the optical path of the measuring light when the image is acquired.

12. The imaging apparatus according to claim 11, further comprising:

a splitting unit configured to split, into lights of different polarizations, the measuring light reflected or scattered by the reflection unit, wherein the polarization control unit controls, based on at least one of lights of different polarizations, polarization of the measuring light.

13. The imaging apparatus according to claim 11, wherein the measurement object is an eye.

14. The imaging apparatus according to claim 11, wherein the control by the polarization control unit is a calibration.

15. An imaging apparatus comprising:

an irradiation optical system configured to irradiate a measurement object with a measuring light, the irradiation optical system including a light source and a first splitting unit configured to split a light emitted from the light source into the measuring light and a reference light;

a generating unit configured to generate a combined light by combining the reference light and the measuring light reflected or scattered by a reflection unit that is configured to reflect or scatter the measurement light;

a polarization control unit configured to control, based on the combined light, polarization of the measuring light; and an image acquisition unit configured to acquire an image of the measurement object, wherein the reflection unit is configured to be placed in an optical path of the measuring light when the polarization control unit controls polarization of the measuring light, the reflection unit is configured to be placed out of the optical path of the measuring light when the image is acquired.

16. The imaging apparatus according to claim 15, further comprising:

a second splitting unit configured to split, into lights of different polarizations, the combined light, wherein the polarization control unit controls, based on at least one of lights of different polarizations, polarization of the measuring light.

17. The imaging apparatus according to claim 15, wherein the measurement object is an eye.

18. The imaging apparatus according to claim 15, wherein the control by the polarization control unit is a calibration.

19. An imaging apparatus comprising:

an irradiation unit configured to irradiate a measurement object with a measuring light;

a polarizing control unit configured to control polarization of the measuring light; and an image acquisition unit configured to acquire an image of the measurement object, wherein a reflection unit is configured to reflect or scatter the measurement light and is configured to, in a first mode which is a mode for controlling polarization of the measuring light by the polarizing control unit, be placed in an optical path of the measuring light, and the reflection unit is configured to, in a second mode which is a mode for acquiring the image, be placed out of the optical path of the measuring light.

20. The imaging apparatus according to claim 19, wherein the measurement object is an eye.

21. The imaging apparatus according to claim 19, wherein the control by the polarization control unit is a calibration.

22. The imaging apparatus according to claim 1, wherein the image is acquired after the polarization of the measuring light has been controlled.

23. The imaging apparatus according to claim 11, wherein the image is acquired after the polarization of the measuring light has been controlled.

24. The imaging apparatus according to claim 15, wherein the image is acquired after the polarization of the measuring light has been controlled.

25. The imaging apparatus according to claim 19, wherein the image is acquired after the polarization of the measuring light has been controlled.

26. The imaging apparatus according to claim 1, wherein the reflection unit is configured to be placed out of the optical path of the measuring light in the second mode after the reflection unit is placed in the optical path of the measuring light.

27. The imaging apparatus according to claim 11, wherein the reflection unit is configured to be placed out of the optical path of the measuring light when the image is acquired after the reflection unit is placed in the optical path of the measuring light.

28. The imaging apparatus according to claim 15, wherein the reflection unit is configured to be placed out of the optical path of the measuring light when the image is acquired after the reflection unit is placed in the optical path of the measuring light.

29. The imaging apparatus according to claim 19, wherein the reflection unit is configured to be placed out of the optical path of the measuring light in the second mode after the reflection unit is placed in the optical path of the measuring light.

* * * * *